United States Patent
Bathina et al.

(10) Patent No.: US 11,439,790 B2
(45) Date of Patent: Sep. 13, 2022

(54) METHOD AND SYSTEM FOR AT LEAST REDUCING OR PREVENTING DELIRIUM IN A PATIENT

(71) Applicant: FUTURE WORLD HOLDINGS LLC, Burlingame, CA (US)

(72) Inventors: Raghu Bathina, Los Altos Hills, CA (US); Sridhar Prathikanti, Burlingame, CA (US)

(73) Assignee: FUTURE WORLD HOLDINGS LLC, Burlingame, CA (US)

( * ) Notice: Subject to any disclaimer, the term of this patent is extended or adjusted under 35 U.S.C. 154(b) by 0 days.

(21) Appl. No.: 16/574,695

(22) Filed: Sep. 18, 2019

(65) Prior Publication Data

US 2021/0077772 A1 Mar. 18, 2021

(51) Int. Cl.
*A61M 21/02* (2006.01)
*A61B 5/16* (2006.01)
*H04N 21/262* (2011.01)
*A61M 21/00* (2006.01)

(52) U.S. Cl.
CPC .......... *A61M 21/02* (2013.01); *A61B 5/165* (2013.01); *A61M 2021/005* (2013.01); *A61M 2021/0027* (2013.01); *H04N 21/26241* (2013.01)

(58) Field of Classification Search
CPC ....... A61M 21/00–02; H04N 21/26241; A61B 5/165
See application file for complete search history.

(56) References Cited

U.S. PATENT DOCUMENTS

| | | | |
|---|---|---|---|
| 2013/0102836 A1* | 4/2013 | Millman | A61M 21/00 600/28 |
| 2013/0165741 A1* | 6/2013 | Seabury | A61M 21/02 600/27 |
| 2014/0181127 A1* | 6/2014 | Van Schijdel | A61M 21/00 707/754 |
| 2015/0294067 A1* | 10/2015 | Kare | G16H 10/60 705/3 |
| 2017/0216555 A1* | 8/2017 | Lutz | A61M 21/00 |
| 2017/0224950 A1* | 8/2017 | Lutz | A61G 10/00 |
| 2018/0333558 A1* | 11/2018 | Levendowski | A61B 5/11 |
| 2019/0160286 A1* | 5/2019 | Yang | G06F 3/011 |
| 2019/0388647 A1* | 12/2019 | Bender | A61M 21/02 |
| 2020/0042160 A1* | 2/2020 | Gabbi | G06F 3/0486 |

(Continued)

OTHER PUBLICATIONS

Malakooti, "Virtual reality experience in the PICU," ICU Management & Practice, vol. 19, issue 2, Summer 2019, p. 94-95. (Year: 2019).*

(Continued)

*Primary Examiner* — Thaddeus B Cox
(74) *Attorney, Agent, or Firm* — HM Law Group LLP; Vani Moodley, Esq.

(57) ABSTRACT

A method and system four delirium therapy is provided. The method comprises selecting immersive content for displaying to a patient who is experiencing delirium, comprising selecting said immersive content from a database based on a time of day attribute associated with the immersive content; and administering the selected immersive content to the patient, by displaying said content to the patient on a display, and simultaneously playing any audio component of said content to the patient.

16 Claims, 12 Drawing Sheets

(56) References Cited

U.S. PATENT DOCUMENTS

2020/0289696 A1* 9/2020 Xie .......................... A61L 9/00

OTHER PUBLICATIONS

Brouk, "ICU patients' recovery to be aided by virtual reality," https://news.iu.edu/stories/2018/04/iupui/inside/26-icu-patients-recovery-to-be-aided-by-virtual-reality.html, Apr. 2018. (Year: 2018).*
Suvajdzic et al., "Developing a Patient-Centered Virtual Reality Healthcare System to Prevent the Onset of Delirium in ICU Patients," 2019 IEEE 7th International Conference on Serious Games and Applications for Health, Aug. 2019. (Year: 2019).*
Turon et al., "Feasibility and safety of virtual-reality-based early neurocognitive stimulation in critically ill patients," Annals of Intensive Care, 7:81, 2017. (Year: 2017).*
Gerber et al., "Visuo-acoustic stimulation that helps you to relax: A virtual reality setup for patients in the intensive care unit," Scientific Reports 7:13228, Oct. 2017. (Year: 2017).*
Suvajdzic et al., Virtual Reality and Human Consciousness: The Use of Immersive Environments in Delirium Therapy, Technoetic Arts, 16(1): 75-83, Mar. 2018. (Year: 2018).*

* cited by examiner

METHOD AND SYSTEM FOR AT LEAST REDUCING OR PREVENTING DELIRIUM IN A PATIENT

FIELD

Embodiments of the present invention relate to a system and method for modulating a patient's sympathetic and parasympathetic response for a medical intervention.

BACKGROUND

Delirium is a significant complication of an intensive care unit (ICU) admission, and can lead to increased lengths of stay, poorer clinical outcomes, increased costs and residual psychological sequelae.

Delirium is a serious condition that results in an acute change in the mental state of critically ill patients, with disturbances to their consciousness, attention, cognition and perception. The condition is caused by multiple factors, but exacerbated by the noise, light, and sleep deprivation experienced in an ICU.

There are number of factors which can lead to this complication, including increased age, severe comorbid conditions, criticality of illness, severe sepsis due to infections, cancer therapy, electrolyte and endocrine disturbances and cerebrovascular, renal and cardiac dysfunction. In addition, withholding of benzodiazepines that could be used for sedation, inadequately relieved pain, alcoholism, smoking and substance abuse can precipitate ICU delirium.

One likely cause for delirium is disturbance in the sleep-wake cycle caused by interrupted sleep and a loss of day/night orientation. This is a common occurrence in hospital rooms and ICUs.

Research has shown that delirium is linked to a disturbance of circadian integrity.

SUMMARY

Embodiments of the present invention disclose a systems and methods for rebalancing a patient's circadian rhythm using immersive content (videos) that correspond to the time of day at the patient's location. The immersive content may comprise general day and night scenes or visuals from the patient's own city or neighborhood.

In use, a virtual reality device is worn by the patient, and client software is started, for example by a clinician. The client software is configured to administer a reorientation protocol adapted to bring the patient out of delirium. In one embodiment, said reorientation protocol comprises exposing the patient a plurality of factors indicative of the current time of day at the patient's locale. Said factors may include imagery and sounds corresponding to the time of day. For example, if the time of day corresponds to the morning, then the imagery may include images and sounds associated with a typical morning, such as a visual of a sunrise, and sounds of birds chirping. On the other hand, if the time of day is 8 PM at night, then a visual of a neighborhood scene, with streetlamps turned on may be provided. Other examples of factors indicative of the current time may also include objects such as clocks, calendars, daily schedules, etc. which may be graphically rendered and superimposed with the visual's. Thus, for example in the case of the above-described morning scene, a clock showing the actual time may be superimposed in the scene in order to provide the patient with a strong indication of the current time.

In one embodiment, noise cancellation technology may be used in order to isolate the patient from the current sound environment thereby to more fully immerse the patient into the sound environment associated with the audiovisual content being provided. Advantageously, said noise cancellation technology may assist the patient in falling asleep for example in noisy/bright environments such as an ICU room with beeping sounds and always on lights and LEDs.

In some embodiments, the immersive experience may comprise audiovisual experiences matching the actual time of day as a morning, afternoon, or an evening. In other embodiments, the immersive experience may comprise audiovisual experiences that simply correspond to day and night scenes.

In one embodiment, the reorientation therapy may comprise exposing the patient to the immersive experience for 15-20 minutes at a time. This may be repeating 2 to 4 times per day on the schedule. In some cases the schedule may comprise a morning viewing, and a nighttime viewing. In other cases the schedule may comprise a morning viewing, and afternoon during, an evening viewing, and night viewing.

Other aspects of the invention will be apparent from the written description below.

DETAILED DESCRIPTION

In the following description, for purposes of explanation, numerous specific details are set forth in order to provide a thorough understanding of the invention.

Reference in this specification to "one embodiment" or "an embodiment" means that a particular feature, structure, or characteristic described in connection with the embodiment is included in at least one embodiment of the invention.

The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not others.

Moreover, although the following description contains many specifics for the purposes of illustration, anyone skilled in the art will appreciate that many variations and/or alterations to said details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

As will be appreciated by one skilled in the art, the aspects of the present invention may be embodied as a system, method or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "module," or "system." Furthermore, aspects of the present invention may take the form of a computer program product embodied in one or more computer readable medium(s) having computer readable program code embodied thereon.

Embodiments of the present invention disclose a system and method to re-orientate a patient suffering from ICU delirium.

Figure 1:
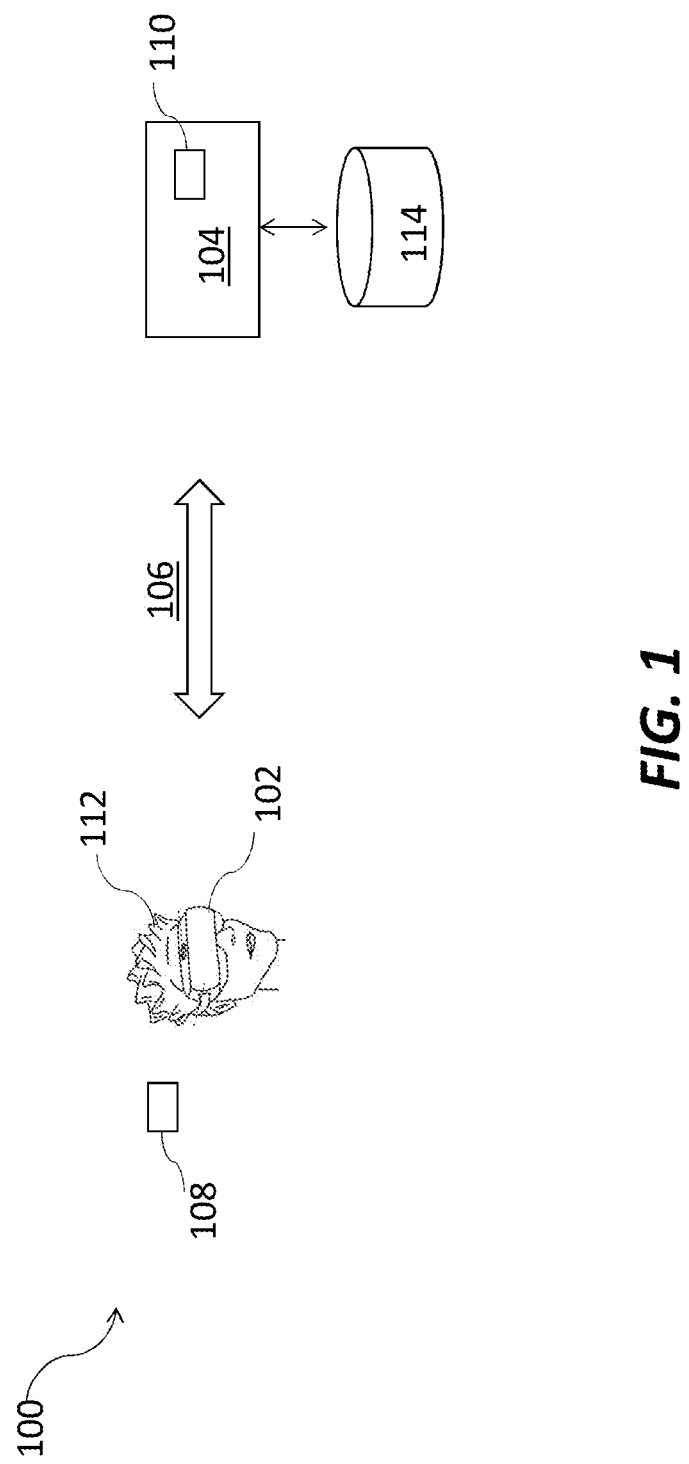
FIG. 1 is a schematic drawing illustrating an implementation of a Patient Response Modulation System 100 in accordance with one embodiment of the invention.

FIG. 1 of the drawings shows an implementation 100 of the inventive system. Referring to FIG. 1, it will be seen that the implementation 100 includes a virtual reality device 102. For example, the virtual reality device may be the device sold under the tradename Oculus Go. The virtual reality device 102 is provisioned with client software 108 configured to rebalance the circadian rhythm of the patient, as will be described As will be seen, the virtual reality device a 102 his communicatively coupled to a server device 104 by means of a communications link 106. In some embodiments, the communications link 106 may comprise an intermediate network, such as the Internet. The server device 104 is provisioned with server software 110 configured to implement functions incorporation with the client software 108 to provide an immersive audiovisual experiences to a patient. Advantageously, the immersive audiovisual experiences are adapted to pull the patient out of delirium, as will be described.

In use, the client software 108 is configured to be run by a clinician and the virtual reality device 102 is worn by the patient 112. In one embodiment, the audiovisual content that is used to generated the audiovisual experiences may be stored in a database 114 which is communicatively coupled to the server device 104.

In one embodiment, the client software 108 is adapted to automatically play immersive audio visual experiences based on the time of the at the patient's locale. Thus, the immersive experiences to which the patient is subjected is synchronized to the local time of day. For example, the client software 108 is configured to play a morning, afternoon, evening or night scene as the case may be based on the actual time of day at the patient's locale. Advantageously, in one embodiment the content available to the client software 108 is indexed based on the time of day.

Figure 2:
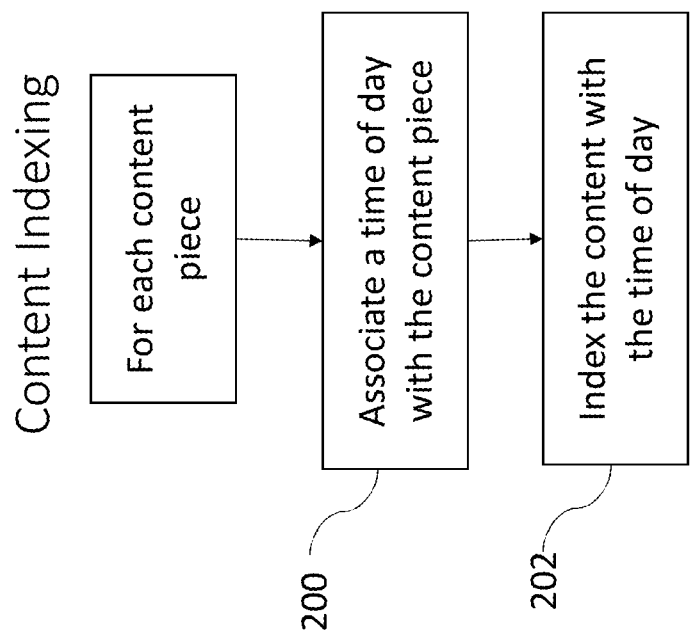
FIG. 2 is a schematic drawing illustrating indexing techniques to index content based on time of day, in accordance with one embodiment of the invention.

Embodiments of the present invention also cover indexing techniques to index content based on time of day. FIG. 2 of the drawings shows the operations involved to index the content according to time of day, in accordance with one embodiment of the invention. Referring to FIG. 2, for each piece of content stored in the database 114, at block 200, a the time of day is associated with said piece of content. For example, if a piece of content includes scenes relating to a morning (such as a sunrise, morning traffic, etc.) then the time of day for that scene will be "morning". At block 202, an index is created comprising each piece of content, and an attribute or tag indicative of the time of day is associated with said piece of content. Thus, by virtue of the mechanism of the index, all pieces of content in the database 114 may be searched to identify content which matches the local time of day.

In some embodiments, the notion of a "time of day" correlates broadly to whether it is day or night.

Advantageously, the immersive content may comprise video scenes shot to provide a 360° immersive view of a scene taking at a particular time of day.

The video content may include outdoor or indoor scenes (typically outdoor to enhance the time of day feeling).

Advantageously, for each scene, there may be provided audio content that is matched to the happenings in the scene (an outdoor market, a busy street, a beach, etc.).

Figure 3:
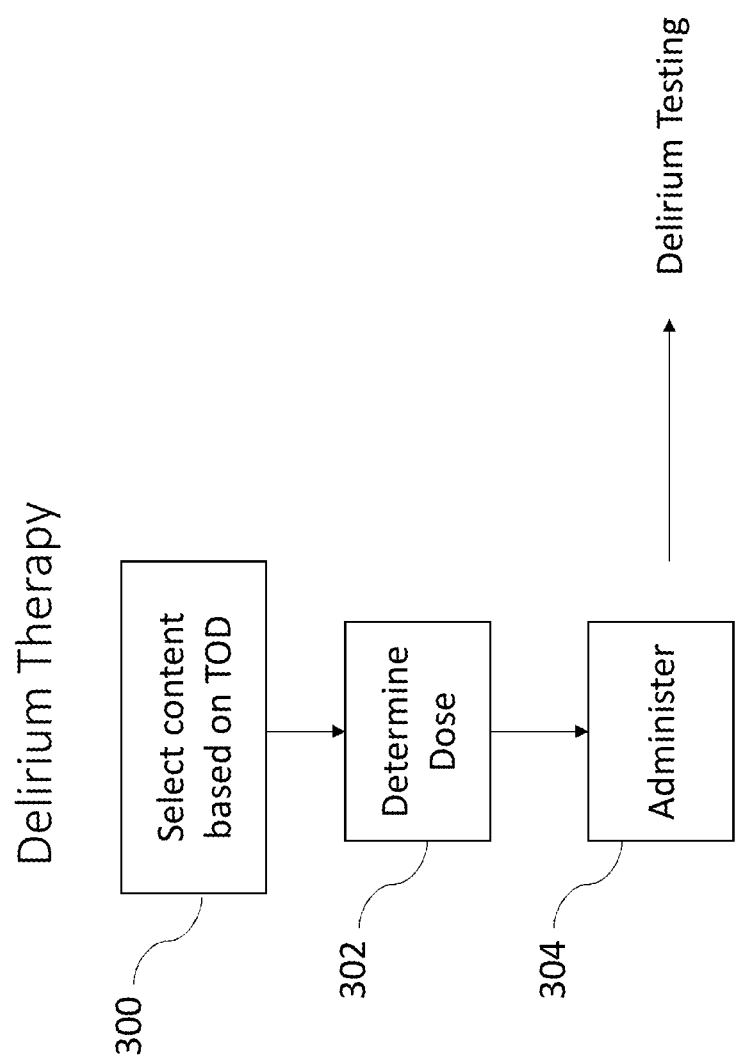
FIG. 3 shows a flow chart of operations performed to deliver an immersive experience, in accordance with one embodiment of the invention.

Referring now to FIG. 3 of the drawings, there is shown a flow chart of operations performed by the client software 108 to administer content to the patient 112. As will be seen, at block 300, operations are performed in order to select content based on the time of day (TOD) at the patient's locale. At block 302, a dose is determined for the content. In one embodiment, the dose may be expressed in terms of a time (for example in minutes, say 20 minutes) for which the selected content is to be administered (shown) to the patient. In some cases, the dose may be determined by the clinician. In other embodiments, the client software 108 may be adapted to determine the dose, as will be described later. At block 304, the dose is administered to the patient 112. This step involves simply showing the selected content to the patient via the virtual reality headset 102. In more advanced embodiments, control from the block 304 optionally then passes to a "delirium testing" loop.

Figure 4:
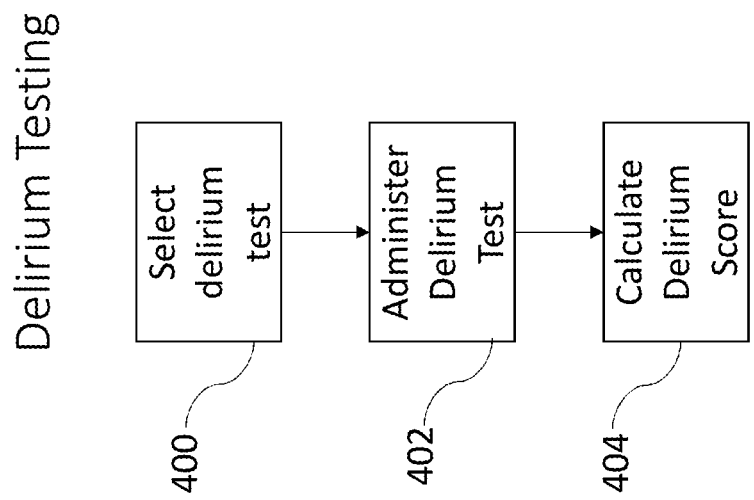
FIG. 4 is a shows a flow chart of operations performed as part of the delirium testing loop, in accordance with one embodiment of the invention.
Figure 5A:
FIG. 5A-B and FIG. 6A-B provides examples of scenes with a graphic to indicate the time, data, and location associated with each scene, in accordance with one embodiment of the invention.
Figure 5B:
Figure 6A:
Figure 6B:

The particular operations performed as part of the delirium testing loop, in accordance with one embodiment is illustrated in the flowchart of FIG. 4. In one embodiment, the database 114 may be provisioned with a plurality of delirium tests, each designed to test a level of delirium experienced by a patient. For example, the delirium tests may be implemented as a series of cognitive and/or motor tests. Referring to FIG. 4, at block 400, a delirium test is selected for the patient. The selection may be based on the patient's age, the patient's locale, and the patient's particular circumstances in terms of whether the patient is in a position to perform motor skills tests. With regard to the latter, the patient may have had surgery that may impede the patient's ability to perform a particular motor test, in which case such a test would be avoided in the selection process.

At block 402, the selected delirium test is administered to the patient by means of the virtual reality device 102. At block 404, the results of the administered delirium test are analyzed, and a delirium score is calculated for the patient. In one embodiment, the score may be normalized to a scale for example in the range 1 to 10 such that the higher the number the more severe the case of delirium. In some embodiments, the analysis of the results of the delirium testing may be performed by the client software 108, whereas in other embodiments it may be performed by the server software 110.

Advantageously, in some embodiments, in addition to indexing the content in the database 114 based on time of day, the content may also be indexed with a searchable attribute indicative of the suitability of the content to be administered to patients with a particular severity of delirium according to the aforementioned delirium score. With indexing of the content in place, in addition to selecting content based on time of day, content may also be selected based on the level of delirium be experienced by the patient.

Once the dose has been administered, the clinician will take off the headset. The dose may be repeated as needed, or on a schedule, or based on the presence of delirium (as indicated by further testing).

In some cases, the immersive content may comprise scenic locations or random locations, for example scenes of the Grand Canyon or London or someone's farm Since familiarity is key driver for curing delirium, showing more familiar scenes can add. Thus, in some embodiments, the audiovisual content may comprise the scenes from the same city or town where the patient is from.

Moreover, the scenes may be from the patient's own neighborhood or immediate surroundings of his or her home (front yard, back yard, etc.)

Scenes may be busy with people talking or they may be placid.

To avoid boredom, the scenes can change on a daily basis or be randomized from a selection of morning scenes (for example)

Finally, the scene need not be real scene, it can also be an animated scene with a sun positioned to the correct location based on the exact time of day The audio portion may be enhanced with head phones Further enhanced with noise-cancellation headphones, earphones, technology that complete block sounds that might otherwise reduce the immersion.

In some embodiments, time of day and location cues can be overlaid in the scenes. These cues may comprise a clock, date and day of the week information, calendar information, and location information.

In some embodiments, the immersive content may be stored locally in the virtual-reality device 102, or it may be stored in the database 114 as described. Moreover, other forms of content indexing may be utilized. For example, the content may be indexed according to famous locations (Golden Gate Bridge, Paris, London, Grand Canyon, etc., and according to particular cities/neighborhoods. These additional scene attributes in the index may be used in the content selection process. For example, the patient may be initially surveyed in order to obtain information on the patient's home neighborhood, and additionally for the cities/places the patient has visited. This information may be used to select content that is indexed with the patient's local neighborhood and/or cities/places the patient has visited. Advantageously, showing the patient scenes from the patient's neighborhood, and/or places the patient has visited correlated by time of day has the potential to accelerate the patient's rehabilitation from ICU.

The audiovisual experience may comprise scenes that may be of some scenic location or random location like the grand canyon or London or someone's farm Since familiarity is key driver for curing delirium, showing more familiar scenes can add value. Thus, in some embodiments, the scenes may be from the same city or town where the patient is from.

Moreover, scenes may be from the patient's own neighborhood or immediate surroundings of his or her home (front yard, back yard, etc.)

In some cases, the scenes may be more engaging with people talking, etc. or they can be less engaging, for example including nature scenes.

In one embodiment, in order to avoid boredom, the scenes may be changed on a daily basis or. Randomized from a selection of morning scenes (for example).

It is important to appreciate that, the scene need not be of real-world objects, comprise animated objects with a sun positioned to the correct location based on the exact time of day.

In use, when a user 112 wants to take a nap, said user puts on the virtual reality device 102, as shown in FIG. 1 and launches the client software 108. Functionally, the client software 108 provides programs that include a plurality of virtual reality environments that are designed to induce, support, or otherwise facilitate sleep. Each of the programs may be customized by a user through a plurality of settings. These settings may be selected by a user or may be provided in the form of a recommendation from the server app/software 110. In one embodiment, the settings may include choices for background music, sleep duration, visual scenes, etc.

Figure 7A:
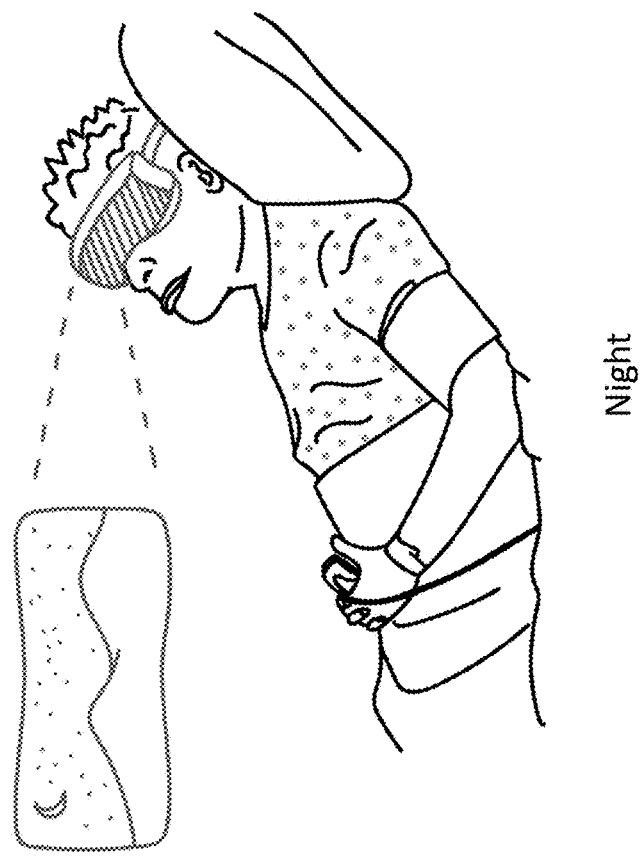
FIG. 7A illustrates a patient in a hospital bed with immersive content being shown to the patient by means of the virtual reality device 102 of FIG. 1, in accordance with one embodiment of the invention.
Figure 7A:
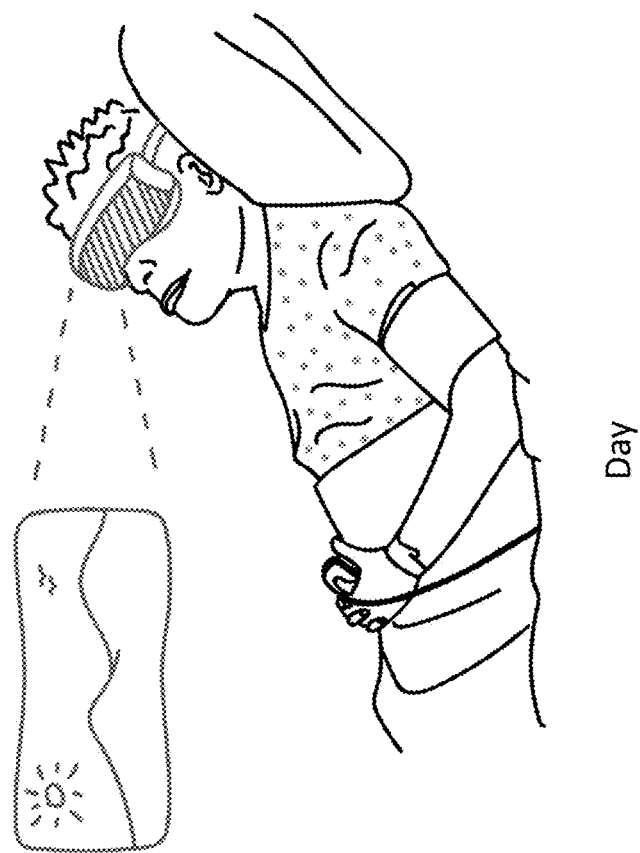
Figure 7B:
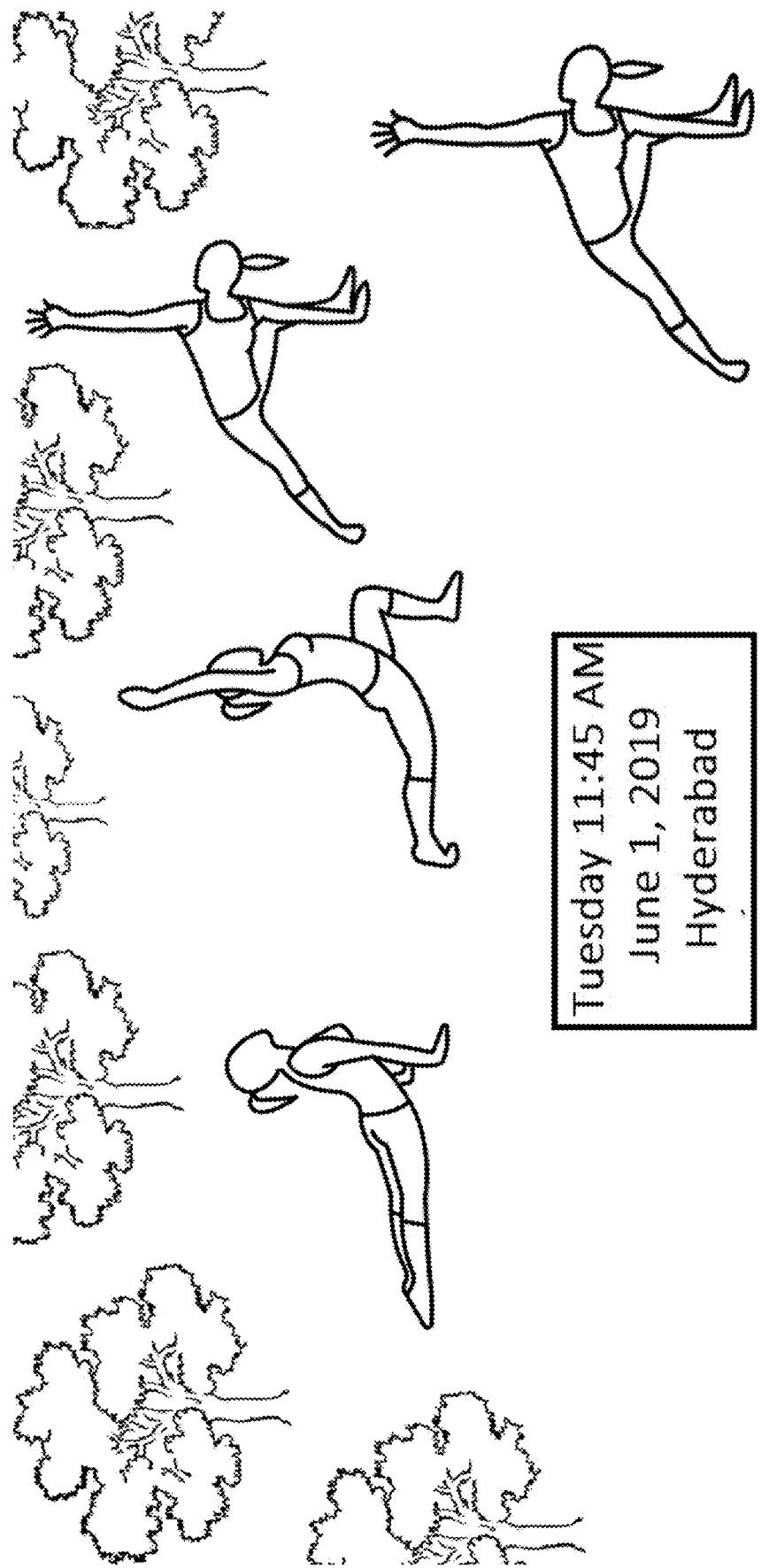
FIG. 7B illustrates an exemplary scenario depicting a women doing yoga in a park with a graphic to indicate the time, date and location associated with the scene, in accordance with one embodiment of the invention.

FIG. 5A-B and FIG. 6A-B provides examples of scenes with a graphic to indicate the time, data, and location associated with each scene. FIG. 7A illustrates a patient in a hospital bed with immersive content being shown to the patient by means of the virtual reality device 102. The patient on the left is shown scenes corresponding to the day, whereas a patient on the right is shown scenes corresponding to the night. Thus although the patient is in the same environment of the hospital, the actual immersive content shown to the patient may be totally decoupled from the actual time of day at the hospital. FIG. 7B illustrates an exemplary scenario depicting a women doing yoga in a park with a graphic to indicate the time, date and location associated with the scene.

Figure 8:
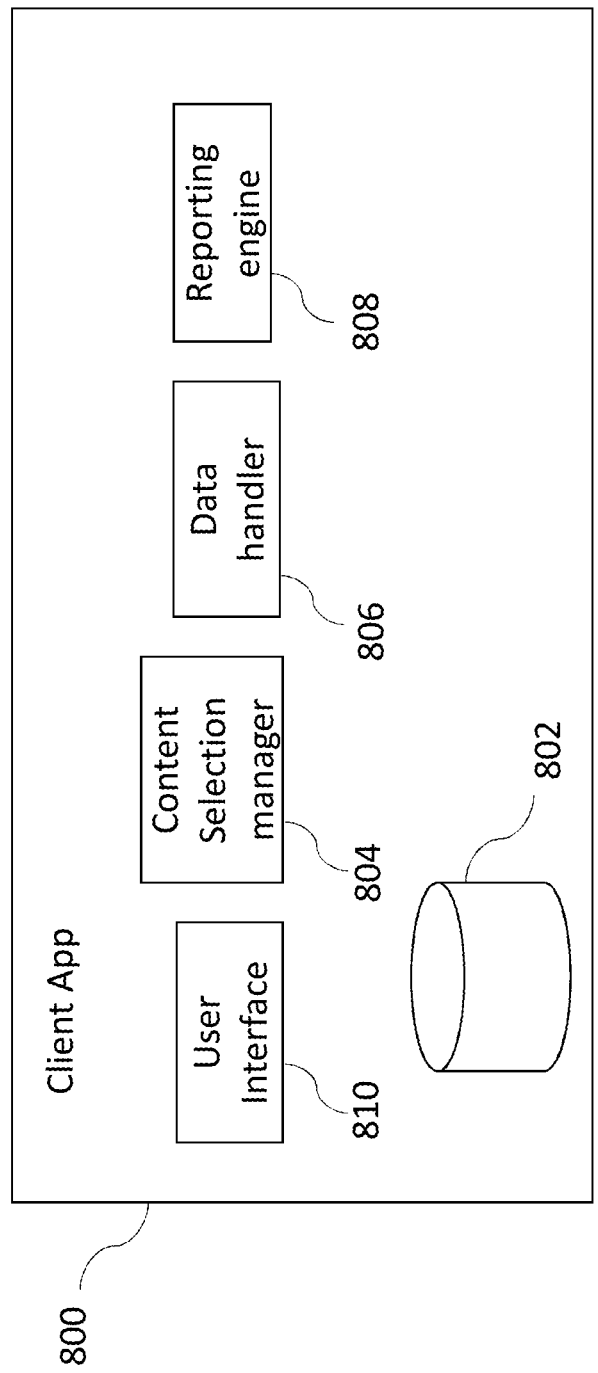
FIG. 8 illustrates a high-level functional block diagram of components of the client software 800, in accordance with one embodiment.

FIG. 8 of the drawings shows a high-level functional block diagram of components of the client software 800, in accordance with one embodiment. As will be seen, the client software 108 may optionally include a database 802 for storing immersive content, and delirium tests.

The client software 800 further comprises a user interface component 810, a content selection manager 804, a data handler 806, and a reporting engine 808. In one embodiment, the user interface 810 may include control to enable the user to select immersive content, the time for which the immersive content is to be shown to a patient, and particular delirium tests to be administered to the patient.

The data handler component 806 is responsible for data exchanges between the client software 800, and the server software 110. Typically, data exchange between these two components include the results of the delirium tests administered to the user.

After a delirium test is executed, user data corresponding to the test is transmitted via the reporting engine 808 to the server software 110 of FIG. 1 via the data handler 806 so that a user profile maintained for the patient by the client/server software 800/110 may be updated.

Figure 9:
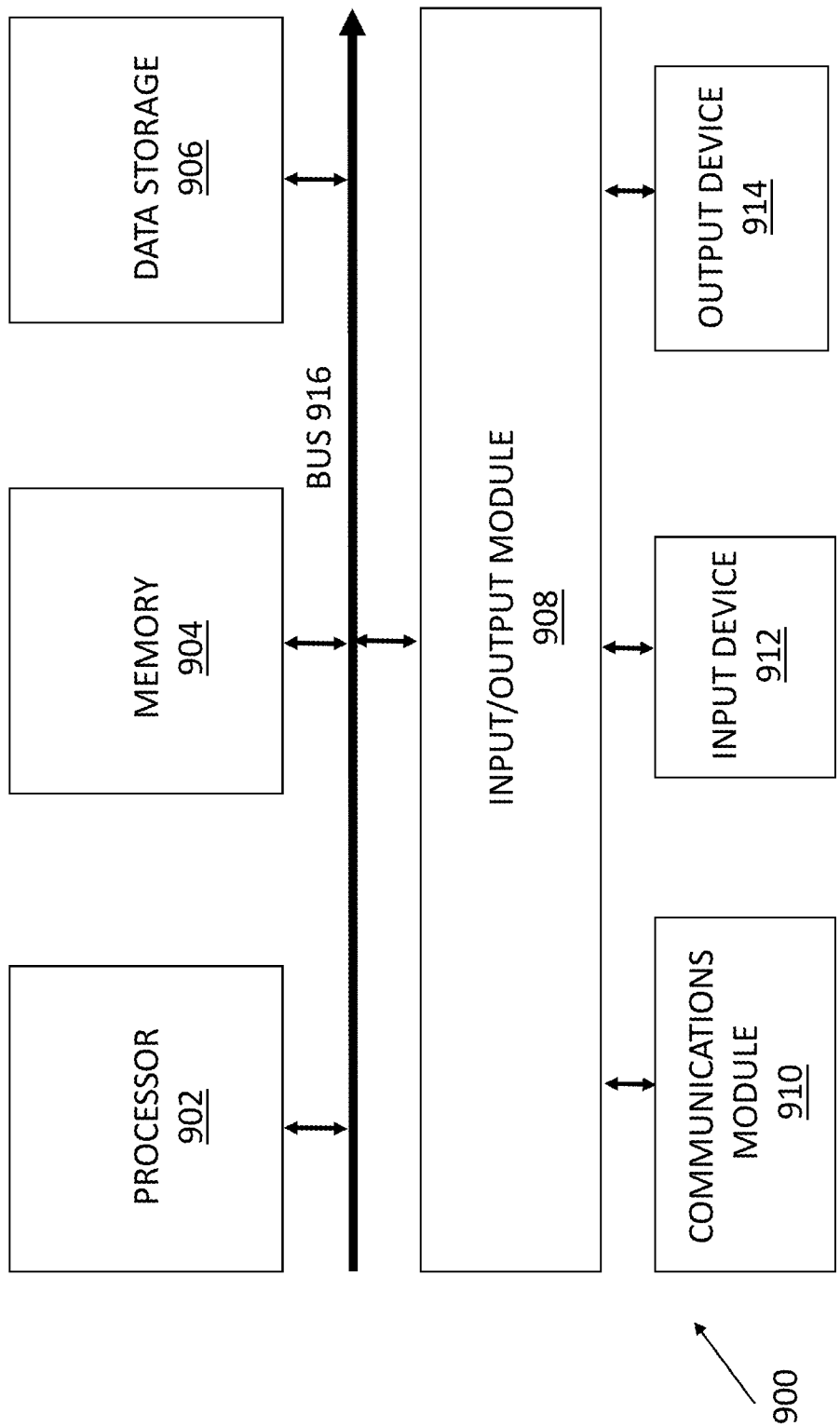
FIG. 9 illustrates a block diagram illustrating exemplary components of the Patient Response Modulation System 100, in accordance with one embodiment of the invention.

FIG. 9 of the drawings shows a high-level functional block diagram 900 illustrating exemplary hardware or the components for the Patient Response Modulation System 100 of FIG. 1 for executing some of the techniques disclosed herein, in accordance with one embodiment of the invention. In certain aspects, the Patient Response Modulation System 100 of FIG. 1 may be implemented using hardware or a combination of software and hardware, either in a dedicated server or integrated into another entity or distributed across multiple entities.

As will be seen, the system 900 includes a communications module 910. The purpose of this module is to maintain communications with the client software 108 of FIG. 1 of each virtual reality device 102 of FIG. 1 that is part of the system. Thus, part of the function of the communications module 902, in one embodiment, is to facilitate a data exchange with each virtual reality device 102 of FIG. 1. Said data exchanges may include sleep data, and sleep session setting recommendations.

The Patient Response Modulation System 900 (e.g., client or server) includes a bus 916 or other communication mechanism for communicating information, and a processor 902 coupled with bus 916 for processing information. According to one aspect, the system 900 is implemented as one or more special-purpose computing devices. The special-purpose computing device may be hard-wired to perform the disclosed techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques. By way of example, the the system 900 may be implemented with one or more processors 902. Processor 902 may be a general-purpose microprocessor, a microcontroller, a Digital Signal Processor (DSP), an ASIC, a FPGA, a Programmable Logic Device (PLD), a controller, a state machine, gated logic, discrete hardware components, or any other suitable entity that can perform calculations or other manipulations of information.

The processor 902 may include, in addition to hardware, code that creates an execution environment for the computer program in question, e.g., code that constitutes processor firmware, a protocol stack, a database management system, an operating system, or a combination of one or more of them stored in an included memory, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 916 for storing information and instructions to be executed by processor 902. The processor 902 and the memory 904 can be supplemented by, or incorporated in, special purpose logic circuitry. Expansion memory may also be provided and connected to the system 900 through input/output module 908, which may include, for example, a SIMM (Single in Line Memory Module) card interface. Such expansion memory may provide extra storage space for the system 900 or may also store applications or other information for the system 900. Specifically, expansion memory may include instructions to carry out or supplement the processes described above and may include secure information also. Thus, for example, expansion memory may be provided as a security module for the system 900 and may be programmed with instructions that permit secure use of the system 900. In addition, secure applications may be provided via the SIMM cards, along with additional information, such as placing identifying information on the SIMM card in a non-hackable manner.

The instructions may be stored in the memory 904 and implemented in one or more computer program products, i.e., one or more modules of computer program instructions encoded on a computer readable medium for execution by, or to control the operation of, the system 900, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, embeddable languages, and xml-based languages. Memory 904 may also be used for storing temporary variable or other intermediate information during execution of instructions to be executed by processor 902.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

The system 900 further includes a data storage device 906 such as a magnetic disk or optical disk, coupled to bus 916 for storing information and instructions. The system 900 may be coupled via input/output module 908 to various devices. The input/output module 908 can be any input/output module. Example input/output modules 908 include data ports such as USB ports. In addition, input/output module 908 may be provided in communication with processor 902, so as to enable near area communication of the system 900 with other devices. The input/output module 908 may provide, for example, for wired communication in some implementations, or for wireless communication in other implementations, and multiple interfaces may also be used. The input/output module 908 is configured to connect to a communications module 910. Example communications modules 910 include networking interface cards, such as Ethernet cards and modems.

The components of the system can be interconnected by any form or medium of digital data communication, e.g., a communication network. The communication network can include, for example, any one or more of a PAN, a LAN, a CAN, a MAN, a WAN, a BBN, the Internet, and the like. Further, the communication network can include, but is not limited to, for example, any one or more of the following network topologies, including a bus network, a star network, a ring network, a mesh network, a star-bus network, tree or hierarchical network, or the like.

For example, in certain aspects, communications module 910 can provide a two-way data communication coupling to a network link that is connected to a local network. Wireless links and wireless communication may also be implemented. Wireless communication may be provided under various modes or protocols, such as GSM (Global System for Mobile Communications), Short Message Service (SMS), Enhanced Messaging Service (EMS), or Multimedia Messaging Service (MMS) messaging, CDMA (Code Division Multiple Access), Time division multiple access (TDMA), Personal Digital Cellular (PDC), Wideband CDMA, General Packet Radio Service (GPRS), or LTE (Long-Term Evolution), among others. Such communication may occur, for example, through a radio-frequency transceiver. In addition, short-range communication may occur, such as using a BLUETOOTH, WI-FI, or other such transceiver.

In any such implementation, communications module 910 sends and receives electrical, electromagnetic or optical signals that carry digital data streams representing various types of information. The network link typically provides data communication through one or more networks to other data devices. For example, the network link of the communications module 910 may provide a connection through local network to a host computer or to data equipment operated by an Internet Service Provider (ISP). The ISP in turn provides data communication services through the world-wide packet data communication network now commonly referred to as the Internet. The local network and Internet both use electrical, electromagnetic or optical signals that carry digital data streams. The signals through the various networks and the signals on the network link and through communications module 910, which carry the digital data to and from the system 900, are example forms of transmission media.

The system 900 can send messages and receive data, including program code, through the network(s), the network link and communications module 910. In the Internet example, a server might transmit a requested code for an application program through Internet, the ISP, the local network and communications module 910. The received code may be executed by processor 902 as it is received, and/or stored in data storage 906 for later execution.

In certain aspects, the input/output module 908 is configured to connect to a plurality of devices, such as an input device 912 and/or an output device 914. Example input devices 912 include a stylus, a finger, a keyboard and a pointing device, e.g., a mouse or a trackball, by which a user can provide input to the system 900. Other kinds of input devices 912 can be used to provide for interaction with a user as well, such as a tactile input device, visual input device, audio input device, brain-computer interface device or a sensory input receptor. For example, feedback provided to the user can be any form of sensory feedback, e.g., visual feedback, auditory feedback, or tactile feedback; and input from the user can be received in any form, including acoustic, speech, tactile, or brain wave input. Example output devices 914 include display devices, such as a LED (light emitting diode), CRT (cathode ray tube), LCD (liquid crystal display) screen, a TFT LCD (Thin-Film-Transistor Liquid Crystal Display) or an OLED (Organic Light Emitting Diode) display, for displaying information to the user. The output device 914 may comprise appropriate circuitry for driving the output device 914 to present graphical and other information to a user.

According to one aspect of the present disclosure, the user systems and the server shown in FIG. 1 can be implemented using the system 900 in response to processor 902 executing one or more sequences of one or more instructions contained in memory 904. Such instructions may be read into memory 904 from another machine-readable medium, such as data storage device 906. Execution of the sequences of instructions contained in main memory 904 causes processor 902 to perform the process steps described herein. One or more processors in a multi-processing arrangement may also be employed to execute the sequences of instructions contained in memory 904. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components.

The system 900 can include clients and servers. A client and server are generally remote from each other and typically interact through a communication network. The relationship of client and server arises by virtue of computer programs running on the respective computers and having a client-server relationship to each other. The system 900 can be, for example, and without limitation, a desktop computer, laptop computer, or tablet computer. The system 900 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer-readable medium" as used herein refers to any medium or media that participates in providing instructions or data to processor 902 for execution. The term "storage medium" as used herein refers to any non-transitory media that store data and/or instructions that cause a machine to operate in a specific fashion. Such a medium may take many forms, including, but not limited to, non-volatile media, volatile media, and transmission media. Non-volatile media include, for example, optical disks, magnetic disks, or flash memory, such as data storage device 906. Volatile media include dynamic memory, such as memory 904. Transmission media include coaxial cables, copper wire, and fiber optics, including the wires that comprise bus 916. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter affecting a machine-readable propagated signal, or a combination of one or more of them.

As used in this specification of this application, the terms "computer-readable storage medium" and "computer-readable media" are entirely restricted to tangible, physical objects that store information in a form that is readable by a computer. These terms exclude any wireless signals, wired download signals, and any other ephemeral signals. Storage media is distinct from but may be used in conjunction with transmission media. Transmission media participates in transferring information between storage media. For example, transmission media includes coaxial cables, copper wire and fiber optics, including the wires that comprise bus 916. Transmission media can also take the form of acoustic or light waves, such as those generated during radio-wave and infra-red data communications. Furthermore, as used in this specification of this application, the terms "computer", "server", "processor", and "memory" all refer to electronic or other technological devices. These terms exclude people or groups of people. For the purposes of the specification, the terms display or displaying means displaying on an electronic device.

To illustrate the interchangeability of hardware and software, items such as the various illustrative blocks, modules, components, methods, operations, instructions, and algorithms have been described generally in terms of their functionality. Whether such functionality is implemented as hardware, software or a combination of hardware and software depends upon the particular application and design constraints imposed on the overall system. Skilled artisans may implement the described functionality in varying ways for each particular application.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

To the extent that the term "include," "have," or the like is used in the description or the claims, such term is intended to be inclusive in a manner similar to the term "comprise" as "comprise" is interpreted when employed as a transitional word in a claim. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase (s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for."

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

The invention claimed is:

1. A computer-implemented method, comprising:
    selecting immersive content, from a database, for displaying to a patient who is experiencing delirium based on a time of day attribute associated with the immersive content;
    administering the selected immersive content to the patient based on a dose, by displaying said immersive content to the patient on a virtual reality device, and simultaneously playing an audio component of said immersive content to the patient;
    administering a delirium test to the patient via the virtual reality device periodically, and analyzing results of the delirium test to quantify a level of delirium experienced by the patient in terms of a delirium score; and
    determining the dose for the patient based on said delirium level, wherein the dose is based on a predefined time for which the immersive content is to be shown to the patient.

2. The method of claim 1, further comprising indexing said immersive content based on a time of day associated with the immersive content.

3. The method of claim 1, further comprising indexing said immersive content with additional attributes selected from the group consisting of neighborhood location, city, tourist destination information, and landmark information.

4. The method of claim 1, wherein the immersive content is selected from the database based on a time of day at the patient's current locale.

5. The method of claim 1, wherein the immersive content is selected from the database based on additional attributes associated with the immersive content including neighborhood information, and landmark information.

6. The method of claim 1, wherein the administering of the selected immersive content comprises superimposing additional cues over a video component of the immersive content adapted to pull the patient out of delirium.

7. The method of claim 6, wherein the additional cues are selected from the group consisting of a timestamp, a date stamp, and location information.

8. The method of claim 1, further comprising using noise cancellation technology to isolate a sound environment to which the patient is exposed such that the patient is only exposed to the audio component associated with the immersive content.

9. A system, comprising:
    a server and database, wherein the server is configured to:
    select immersive content, from the database, for displaying to a patient who is experiencing delirium based on a time of day attribute associated with the immersive content;
    administer the selected immersive content to the patient based on a dose, by displaying said immersive content to the patient on a virtual reality device, and simultaneously playing an audio component of said content to the patient;
    administer a delirium test to the patient via the virtual reality device periodically, and analyze results of the delirium test to quantify a level of delirium experienced by the patient in terms of a delirium score; and
    determine the dose for the patient based on said delirium level, wherein said dose is a defined time for which the immersive content is to be shown to the patient.

10. The system of claim 9, wherein the server is further configured to index said immersive content based on a time of day associated with the immersive content.

11. The system of claim 9, wherein the server is further configured to index said immersive content with additional attributes selected from the group consisting of neighborhood location, city, tourist destination information, and landmark information.

12. The system of claim 9, wherein the immersive content is selected from the database based on a time of day at a patient's locale.

13. The system of claim 9, wherein the immersive content is selected from the database based on additional attributes associated with the immersive content including neighborhood information, and landmark information.

14. The system of claim 9, wherein the selected immersive content administered comprises additional cues superimposed over a video component of the immersive content adapted to pull the patient out of delirium.

15. The system of claim 9, wherein the server is further configured to use noise cancellation technology to isolate a sound environment to which the patient is exposed such that the patient is only exposed to the audio component associated with the immersive content.

16. A non-transitory computer readable storage medium, having stored thereon, a set of computer-executable instructions that cause a computer to perform steps comprising:
    selecting immersive content, from a database, for displaying to a patient who is experiencing delirium based on a time of day attribute associated with the immersive content;
    administering the selected immersive content to the patient based on a dose, by displaying said immersive content to the patient on a virtual reality device, and simultaneously playing an audio component of said immersive content to the patient;
    administering a delirium test to the patient via the virtual reality device periodically, and analyzing results of the delirium test to quantify a level of delirium experienced by the patient in terms of a delirium score; and
    determining the dose for the patient based on said delirium level, wherein the dose is a predefined time for which the immersive content is to be shown to the patient.

* * * * *